(12) United States Patent
Nettleton-Hammond et al.

(10) Patent No.: US 10,085,442 B2
(45) Date of Patent: Oct. 2, 2018

(54) AGROCHEMICAL FORMULATION

(71) Applicant: SYNGENTA PARTICIPATIONS AG, Basel (CH)

(72) Inventors: John Henry Nettleton-Hammond, Bracknell (GB); Niall Rae Thomson, Bracknell (GB); Dirk Armand Wim Stanssens, Houthalen (BE)

(73) Assignee: SYNGENTA PARTICIPATIONS AG, Basel (CH)

( * ) Notice: Subject to any disclaimer, the term of this patent is extended or adjusted under 35 U.S.C. 154(b) by 31 days.

(21) Appl. No.: 15/302,242

(22) PCT Filed: Apr. 28, 2015

(86) PCT No.: PCT/EP2015/059233
§ 371 (c)(1),
(2) Date: Oct. 6, 2016

(87) PCT Pub. No.: WO2015/165916
PCT Pub. Date: Nov. 5, 2015

(65) Prior Publication Data
US 2017/0086454 A1    Mar. 30, 2017

(30) Foreign Application Priority Data
Apr. 28, 2014    (GB) .................................. 1407384.5

(51) Int. Cl.
| A01N 25/04 | (2006.01) |
| A01N 25/10 | (2006.01) |
| A01N 25/28 | (2006.01) |
| A01N 43/54 | (2006.01) |
| A01N 37/36 | (2006.01) |

(52) U.S. Cl.
CPC ............. *A01N 25/04* (2013.01); *A01N 25/10* (2013.01); *A01N 25/28* (2013.01); *A01N 37/36* (2013.01); *A01N 43/54* (2013.01)

(58) Field of Classification Search
CPC ...................................................... A01N 25/04
See application file for complete search history.

(56) References Cited

U.S. PATENT DOCUMENTS

| 4,812,244 A | 3/1989 | Lawson et al. | |
| 2009/0197809 A1* | 8/2009 | Anderson | A01N 43/36 514/3.3 |
| 2011/0257166 A1* | 10/2011 | Damaceno | A01N 37/50 514/229.2 |
| 2014/0106964 A1 | 4/2014 | Jogikalmath et al. | |

FOREIGN PATENT DOCUMENTS

WO    2012048176 A2    4/2012

OTHER PUBLICATIONS

International Search Report for International Application PCT/EP2015/059233 dated Jun. 9, 2015.

* cited by examiner

*Primary Examiner* — Benjamin Packard

(57) ABSTRACT

The present invention relates to a composition comprising an aqueous continuous phase; a first dispersed phase which comprises styrene-maleimide copolymer particles; and a second dispersed phase which is either oil droplets, suspended particles or a capsule suspension; and to use of those compositions to control agricultural pests or diseases. It also relates to use of such compositions where rainfastness is important.

13 Claims, No Drawings

AGROCHEMICAL FORMULATION

RELATED APPLICATION INFORMATION

This application is a 371 of International Application No. PCT/EP2015/059233, filed Apr. 28, 2015, which claims priority to GB Application 1407384.5, filed Apr. 28, 2014, the contents of which are incorporated herein by reference herein.

The present invention relates to compositions comprising an aqueous continuous phase; a first dispersed phase which comprises styrene-maleimide co-polymer particles; and a second dispersed phase which is either oil droplets, suspended particles or a capsule suspension; in particular it relates to such compositions in the agrochemical field; and to use of those compositions to control agricultural pests or diseases. It also relates to use of such compositions where rainfastness is important.

The main application of agrochemical active ingredients is by spray application, often foliar spray application, but this means that the agrochemical may be subject to a variety of loss mechanisms before it is able to reach its intended site of action in, say, a weed, insect or fungus. The main causes of loss of an agrochemical include rainwashing, photodegradation and insufficient retention on the intended surface. There is therefore a need to be able to improve the physiochemical characteristics of sprayed agrochemical deposits such that subsequent to good retention of the sprayed deposit on a surface, for example a leaf surface, the agrochemical is not washed off by any rain and is not degraded by sunlight, yet the agrochemical must nevertheless remain bioavailable so as to kill or control any unwanted pests [including weeds, fungi, insects and nematodes].

A variety of adjuvants have been proposed and used in the past, seeking to improve rainfastness and u.v. protection. WO2012048176 discloses an array of polymer types that may be used to improve herbicide performance as a soil application (rather than a foliar application) and is dependent upon intimate systems in which pi-pi stacking is possible but this document is not concerned with rainfastness.

The use of polymers to encapsulate active ingredients and alter release rates under a range of conditions is well known (a good summary is provided by WO02/100525, in particular pages 2 to 4)—examples include polyurea walls as described in U.S. Pat. No. 4,280,833. Vive Nano's WO10035118 gives a further example where poly(acrylic acid), poly(methacrylic acid) and poly(styrene sulfonate) are used to encapsulate active ingredients.

WO2012/048176 teaches the encapsulation of an agrochemical with an SMI polymer, where the encapsulation unsurprisingly alters the properties of the active ingredients. To achieve the encapsulation the SMI polymer must first be dissolved by lowering the pH of an aqueous dilution, the active ingredient is then encapsulated by the polymer when the pH is raised; as described in WO2012/048176 example 6 and is typical for polymer encapsulation processes. WO2012/048176 goes to great length to teach how the SMI could be intimately linked to achieve encapsulation but at no point foresees the application of dispersed SMI polymer within an aqueous continuous phase with a second, completely separate, dispersed phase. Surprisingly we have now found that advantageous properties can be gained by forming such a two part dispersion.

We have now unexpectedly and surprisingly achieved improved rainfastness of biologically active ingredients through the use of a styrene-maleimide co-polymer, which is formulated as an aqueous dispersion of particles which comprise a styrene-maleimide co-polymer. Furthermore, not only may rainfastness of a biologically active ingredient be improved but the biological activity of that active ingredient, and possibly accompanying active ingredients, may be uncompromised (or not significantly compromised). Accordingly, by reducing loss of an active ingredient, the biological effect of a particular dose of that active ingredient may be increased or the biological effect may be prolonged. At the same time, the uptake or biological effect of any partner active ingredient may be unimpaired.

The aqueous dispersion of particles of a styrene-maleimide co-polymer may therefore comprise a suspension of solid particles of an agrochemical in the continuous aqueous phase; or alternatively the agrochemical may be present as an oil which is dispersed as emulsion droplets in the continuous aqueous phase; or an agrochemical may even be dissolved in an oil which is dispersed as emulsion droplets in the continuous aqueous phase; or an agrochemical may be contained within capsules (microcapsules) suspended in the continuous aqueoeus phase. The suspended particles, emulsion droplets or suspended capsules will have conventional dimensions (that is, typically of the order of one to ten microns). Such a formulation approach provides both the styrene-maleimide co-polymer and an agrochemical together in a single formulation, which may be applied either directly to a target or may be diluted in a conventional spray tank before being sprayed onto a target. When applied via a spray tank, other conventional adjuvants [such as surfactants or oil adjuvant compositions] may be added to the spray tank prior to spraying.

Alternatively, the aqueous dispersion of particles of a styrene-maleimide co-polymer may comprise an emulsion of an oil adjuvant (that is, a lipophilic bioperformance enhancing adjuvant), whereby oil droplets are dispersed in the continuous aqueous phase. Suitably the oil adjuvant may be selected from mineral oils, vegetable oils, derivatives thereof and also plasticiser adjuvants. Such a composition may then be added to a conventional spray tank, to be diluted in water along with a separate formulation containing an agrochemical (of course, that formulation could also be a formulation according to the present invention, as described above) prior to spraying. Examples of commercially available tank mix adjuvants include the mineral oil based Nimbus™ and non-ionic wetting agent Activator 90™.

Furthermore, an aqueous dispersion according to the present invention may be provided within a conventional spray tank, for example by adding, say, both a conventional agrochemical suspension concentrate formulation and a styrene-maleimide co-polymer dispersion to water in the spray tank.

Therefore the present invention provides a composition comprising:
(i) an aqueous continuous phase;
(ii) a first dispersed phase which is particles which themselves comprise a styrene-maleimide co-polymer; and
(iii) a second dispersed phase which is either droplets comprising an oil; is suspended solid particles; or is a capsule suspension.

Clearly, both dispersed phases (ii) and (iii) are each dispersed in continuous phase (i). Accordingly the present invention provides a composition comprising:
(i) an aqueous continuous phase;
(ii) a first dispersed phase dispersed in (i) which is particles which themselves comprise a styrene-maleimide co-polymer; and (iii) a second dispersed phase dispersed in (i) which is either droplets comprising an oil; is suspended solid particles; or is suspended capsules.

Capsules may be conventional microcapsules which comprise a polymer shell wall within which there is a core, which may be solid but is more suitably a liquid core.

The styrene-maleimide co-polymer particle may be a random co-polymer or a block co-polymer; preferably is a random co-polymer.

In one aspect, the present invention provides a composition as above where the second dispersed phase comprises an agrochemical where the agrochemical is either the suspended solid particles; is in the oil droplets; or is present within capsules of the capsule suspension; and in an alternative aspect, the present invention provides a composition as described above where the second dispersed phase is droplets of an oil adjuvant.

Furthermore, the continuous aqueous phase may contain both an emulsified oil adjuvant, as described above, and an agrochemical as described above [that is, the agrochemical is either in suspended, emulsified or encapsulated form].

The composition of the present invention may also contain conventional formulation aids, such as suspending agents, wetting agents, emulsifying agents, antifoams, antifreeze agents, pH adjusters, buffers and viscosity control agents. It is also possible for a water soluble agrochemical to be dissolved in the aqueous continuous phase.

The styrene-maleimide co-polymer particles may be prepared by known methods.

The styrene-maleimide co-polymer particle may be a random co-polymer or a block co-polymer and may be prepared from cyclic anhydrides and vinyl monomer units, which have been subjected to an imidization reaction wherein the degree of imidization is below 90%.

Those skilled in the art will know that styrene-maleimide copolymers and dispersions thereof can be prepared by a number of routes, such as those discussed in Hanson and Zimmerman, Ind. Eng. Chem. Vol 49 nr. 11 (1957), p. 1803-1807, WO 2000/34362, WO2011/098574 and that the co-polymer may be present in a core/shell system, as discussed in WO2011/110498.

Suitable monomers for the polymer are for example α-β-unsaturated dicarboxylic anhydrides such as maleic anhydride, alkyl or alkenyl maleic anhydrides, citraconic anhydride, itaconic anhydride and mixtures thereof. Preferably the co-polymer contains maleic anhydride monomer units.

Suitable vinyl monomers for use in the co-polymer include vinyl aromatic monomers (such as styrene, α-methyl styrene, vinyl toluene and indene) and mono-olefinic unsaturated hydrocarbons (such as ethylene, propylene and isobutylene) (for example, please see WO2011/098574).

The anhydride monomer content of the co-polymer may be from 15 to 50 mole %, preferably from 15 to 43 mole %, more preferably from 20 to 36 mole % and most preferably from 22 to 32 mole %; and the vinyl monomer content of the co-polymer may be from 85 to 50 mole %; preferably from 85% to 67%; more preferably from 80 to 67 mole %.

The co-polymer has a weight averaged molecular weight (Mw) ranging from 4000 to 500000 g/mole, preferably from 10000 to 300000 g/mole, more preferably from 8000 to 12000 g/mole as determined by gel permeation chromatography using a polystyrene standard in tetrahydrofuran.

The styrene maleimide random or block copolymer is insoluble in water and will form a dispersion, with the size (average diameter) of the primary particles ranging from 20-200 nm, and an average particle diameter being 70-100 nm as determined by light scattering measurements. Preferably the average is the $D_{50}$ average. Those skilled in the art will be aware that the primary particles can form agglomerates.

The styrene maleimide random (or block) copolymer structure may be defined by the general structure in formula (1)

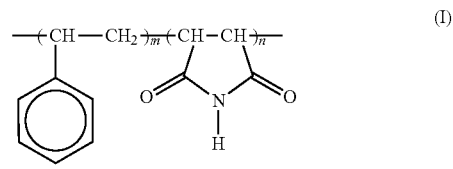

where m, the number average of vinyl units is from 250 to 800; and n, the number average of cyclic anhydride units, is from 100 to 400. More preferably m is from 550 to 575; and n is from 200 to 225.

The particles may be composed entirely of a styrene-maleimide co-polymer or may be just partially styrene-maleimide co-polymer. When the polymerisation is carried out in the presence of another water insoluble species (that is a second component, such as wax or oil), the second component can be encapsulated. In the case where the core is a wax, paraffin wax can be used. In the case where a shell of the copolymer is formed around the oil, suitable oils include mineral oils; vegetable oils and esters of vegetable oils (for example, please see WO2011/098574). Such a core may comprise an oil and such an oil may provide bioperformance advantages for an agrochemical (that is, it may be an oil adjuvant, as discussed above). An example of such an oil is soybean oil. An example of such a commercially available styrene maleimide copolymer which contains soybean oil is Nanotope™ 26 SO50 WA50-30 which is used in the examples herein. The ratio of the oil in the core to the co-polymer may be from 70:30 to 30:70 (preferably about 50:50) by weight.

The concentration of the styrene-maleimide co-polymer in the composition is preferably from 2 to 50% by weight; more preferably from 3 to 30%; even more preferably from 4 to 10% by weight.

In one aspect, the present invention provides the use of a core/shell styrene-maleimide co-polymer with an agrochemical.

The term agrochemical includes herbicides, fungicides, insecticides, neamticides and plant growth regulators. Suitably an agrochemical is an herbicide, a fungicide, a nematicide or an insecticide; more suitably it is an herbicide, a fungicide or an insecticide; even more suitably it is a fungicide or an insecticide.

Examples of agrochemical active ingredients suitable for use within the continuous phase (i) or disperse phase (iii) in accordance with the present invention include, but are not limited to: fungicides such as azoxystrobin, chlorothalonil, cyprodinil, cyproconazole, difenoconazole, fludioxonil, mandipropamid, picoxystrobin, propiconazole, pyraclostrobin, tebuconazole, thiabendazole, trifloxystrobin, bixafen, fluxapyroxad, furametpyr, isopyrazam, penflufen, penthiopyrad, sedaxane, boscalid, fenfuram, benofanil, flurtolanil, mepronil, thifluzamide, carboxin, oxycarboxin, acidbenxolar-S-methyl, oxathiapiprolin; and insecticides such as carbamates such as aldicarb, bendiocarb, benfuracarb, carbaryl, carbofuran, carbosulfan, fenoxycarb, fenobucarb, methiocarb, methomyl, oxamyl, pirimicarb, thiodicarb, triazamate; organophosphates such as acephate, chlorpyrifos, diazinon, malathion, methamidophos, methidathion, monocrotophos, parathion-methyl, pirimiphos-methyl, profenofos, terbufos; fiproles such as ethiprole, fipronil;

pyrethroids such as allethrin, bifenthrin, cyfluthrin, cyhalothrin, cypermethrin, alpha-cypermethrin, beta-cypermethrin, zeta-cypermethrin, deltamethrin, esfenvalerate, etofenprox, fenvalerate, lambda-cyhalothrin, permethrin, pyrethrin, tau-fluvalinate, tefluthrin, tetramethrin; neonicotinoids such as clothianidin, dinotefuran, flupyradifurone, imidacloprid, thiamethoxam, nitenpyram, acetamiprid, thiacloprid;

spinosyns such as spinosad, spinetoram;

avermectins such as abamectin, emamectin benzoylureas such as buprofezin, chlorfluazuron, cyramazin, clofentazine, diflubenzuron, diofenolan, etoxazole, flucycloxuron, flufenoxuron, hexaflumuron, lufenuron, novaluron, teflubenzuron, triflumuron;

tetronic and tetramic acid derivatives such as spirodiclofen, spiromesifen, spirotetramat; pymetrozine, flonicamid, etoxazole, indoxacarb;

ryanoids such as cyantraniliprole.

Preferably the agrochemical is a contact agrochemical (rather than a systemic agrochemical).

Suitable fungicides may be selected from azoxystrobin, chlorothalonil, cyprodinil, difenoconazole, fludioxonil, mandipropamid, picoxystrobin, pyraclostrobin and trifloxystrobin. Preferably the fungicide is a strobilurin; more preferably it is azoxystrobin.

Suitable insecticides may be selected from abamectin, clothianidin, emamectin benzoate, gamma cyhalothrin, cyhalothrin and its enantiomers such as lambda cyhalothrin, tefluthrin, permethrin, resmethrin and thiamethoxam.

Preferably, when the composition of the present invention contains an agrochemical [such as a strobilurin] it further contains a triazole fungicide such as cyproconazole, difenoconazole, propiconazole or tebuconazole.

Preferably the total agrochemical concentration in the composition is from 5% to 40% by weight; more preferably from 15% to 30%.

The compositions of the present invention may be used to improve the rainfastness of an agrochemical.

The compositions of the present invention may be used to combat or control an agricultural pest or disease [such as a weed, a fungus, a nematode or an insect].

Stable compositions according to the present invention can be prepared readily using standard techniques, without having to take any special measures.

The present invention is illustrated by the following examples. The styrene maleimide copolymer used in all the following examples was Nanotope™ 26 SO50 WA50-30, supplied by TopChim.

Suitable agrochemicals are azoxystrobin, cyproconazole, isopyrazam, cyantranilipole and chlorothalonil, as shown by the examples.

EXAMPLE 1

Improved rainfastness of azoxystrobin with styrene maleimide copolymer on corn.

This study demonstrates that the addition of styrene maleimide copolymer can reduce the loss of an active ingredient from a leaf surface during rainfall.

A range of substrates can be used in this test with the chosen material in this example being a maize leaf. Herein the maize plants, avenir variety, were grown for 3 weeks to the 5 leaf stage. These leaves were mounted using double sided tape to flat tiles (30 cm by 30 cm at an even spacing of 3 leaves per tile.

A deposition solution was then prepared at the concentration which would be used under commercial application conditions. In this case 0.67 g of an azoxystrobin 200 g/l SC formulation and 0.25 g Activator 90™ (non-ionic surfactant) were added to 98.58 g water for the control and the effect of the styrene malemide polymer determined by creating a similar sample with 0.3% w/w of the water replaced by styrene malemide copolymer.

Twenty 0.2 µl droplets were applied to each substrate using a micro applicator. The substrate was allowed to dry for 2 hours. After the drying period one board containing 6 leaves per treatment were 'rained on', at 10 mm/hour for one hour while the other board was sampled by washing each leaf with 20 mls of acetonitrile (Sigma Aldrich) and gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 20 ml acetonitrile for 20 seconds).

The quantities of azoxystrobin in the acetonitrile solutions were determined via LCMS (Thermo TSQ Quantum LC/MS/MS, Column 845) and the % active ingredient remaining after rainfall was determined by dividing the quantity of azoxystrobin on each leaf after rainfall by that before rainfall.

Azoxystrobin SC+Activator 90™: 3.5% azoxystrobin remained on the leaves.

Azoxystrobin SC+Activator 90™+styrene malemide copolymer: 29% azoxystrobin remained on the leaves.

EXAMPLE 2

Improved rainfastness of azoxystrobin with styrene maleimide copolymer on soya.

This study demonstrates that the addition of styrene malemide copolymer can reduce the loss of an active ingredient from a leaf surface during rainfall.

A range of substrates can be used in this test with the chosen material in this example being a soya leaf. Herein the soya, *Glycine Max* (Williams variety), was grown for 4 weeks in 4 inch pots with the top 2 tri-foliates used in the study. The leaves were mounted using double sided tape to flat tiles (30 cm by 30 cm) at an even spacing of 6 leaves per tile.

A deposition solution was then prepared at the concentration which would be used under commercial application conditions. In this case 0.375 g of an azoxystrobin SC formulation (containing 200 g/l azoxystrobin) and 7.5 g Nimbus™ were added to 98.6 g water for the control and the effect of the styrene malemide co-polymer determined by creating a similar sample with 0.3% w/w of the water replaced by styrene malemide co-polymer.

Twenty 0.2 µl droplets were applied to each substrate using a micro applicator. The substrate was allowed to dry for 2 hours. After the drying period one board containing 6 leaves per treatment were 'rained on', at 10 mm/hour for one hour while the other board was sampled by washing each leaf with 20 mls of acetonitrile (Sigma Aldrich) and gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 20 ml acetonitrile for 20 seconds).

The quantities of azoxystrobin in the acetonitrile solutions determined via LCMS (Thermo TSQ Quantum LC/MS/MS, Column 845) and the % active ingredient remaining after rainfall determined by dividing the quantity of AZ on each leaf after rainfall by that before rainfall.

Azoxystrobin SC+Nimbus™: 15% azoxystrobin remained on the leaves.

Azoxystrobin SC™+Nimbus™: styrene malemide copolymer 55% remained on the leaves.

EXAMPLE 3

This example demonstrates that while acrylic polymers known for their water barrier properties can improve the rainfastness of the active ingredient they can also, disadvantageously, reduce the bioavailability.

The method described in Example 2 was used to assess the rainfastness of azoxystrobin in the presence of Nimbus™ on Soya leaves with the addition of various polymers. The acrylic emulsion used was Neocryl™ XK-230 (DSM) and the acrylic latex (Neocryl™ XK-90).

The bioavailability of the azoxystrobin was assessed by spraying three week old soya plant (William's variety) using a track sprayer and a standard flat fan nozzle at an equivalent water volume of 50 l/ha containing 9 g/ha of azoxystrobin, 30 g/ha Nimbus™ and 0.3% w/w of the tested copolymers. The plants were inoculated with $10^5$ spores per ml of water one day after spray application and the first tri-foliates were assessed for fungal control after a further 14 days.

TABLE 1

| Compound | % of azoxystrobin remaining on the leaf surface | % control of *Phakapsora pachyrhizia* |
| --- | --- | --- |
| none | 15 | 100 |
| Styrene Maleimide copolymer | 55 | 100 |
| Acrylic emulsion | 66 | 11 |
| Acrylic latex | 20 | 43 |

The data within the table show that while polymers improve the rainfastness of azoxystrobin surprisingly only the styrene maleimide allows the active ingredient to deliver acceptable biological performance.

EXAMPLE 4

This example demonstrates the lack of impact on uptake of cyproconazole by the styrene maleimide copolymer.

4" pots of soya, Williams's variety, were grown in the glasshouse for four weeks until the plants reached the 3-4 trifoliate stage. These plants were tracksprayed with the treatment list below at a rate of 24 g a.i./ha in a water volume of 80 l/ha. All treatments included Nimbus™ at a rate of 600 ml/ha.

At time zero, 5 hours after application and 1, day after fully expanded leaves were cut off, weighed and shaken in 10 ml of acetonitrile to remove the unabsorbed foliar deposits. Ten replicate leaves were sampled per treatment and the samples analysed by LCMS (Thermo TSQ Quantum LC/MS/MS, Column 845).

TABLE 2

| Compound | % of cyproconazole within the plant (5 hours after application) | % of cyproconazole within the plan (1 day after application) |
| --- | --- | --- |
| Cyproconazole 80g/l SC + NIMBUS | 67 | 92 |
| Cyproconazole 80g/l SC + Styrene Maleimide copolymer + NIMBUS | 73 | 87 |
| Cyproconazole 80g/l SC + Acrylic latex + NIMBUS | 45 | 78 |

The treatment containing the acrylic latex is has a statistically significant lower uptake of cyproconazole than the treatments containing no additional polymer and the styrene maleimide copolymer, which are statistically equivalent.

EXAMPLE 5

Effect of styrene maleimide rate on the rainfastness of an azoxystrobin 200 g/l SC.

This study demonstrates that the amount of styrene malemide copolymer used positively correlates with the rainfastness of the resulting azoxystrobin-containing formulation.

A range of substrates can be used in this test with the chosen material in this example being a soya leaf. Herein the soya, *Glycine Max*, was grown for 4 weeks in 4 inch pots with the top 2 tri-foliates used in the study. The leaves were mounted using double sided tape to flat tiles (30 cm by 30 cm) at an even spacing of 6 leaves per tile.

A deposition solution was then prepared at the concentration which would be used under commercial application conditions. In this case 0.2 g of an azoxystrobin SC formulation (containing 200 g/l azoxystrobin) and 0.4 g Nimbus™ were added to 99.4 g water for the control and the effect of the styrene maleimide co-polymer determined by creating similar samples with 0.003, 0.006, 0.06, 0.12, 0.30% w/w of the water replaced by styrene malemide co-polymer.

Twenty 0.2 µl droplets were applied to each substrate using a micro applicator. The substrate was allowed to dry for 2 hours. After the drying period one board containing 6 leaves per treatment were 'rained on', at 10 mm/hour for one hour while the other board was sampled by washing each leaf with 20 mls of acetonitrile (Sigma Aldrich) and gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 20 ml acetonitrile for 20 seconds).

The quantities of azoxystrobin in the acetonitrile solutions determined via LCMS (LC/MS/MS comprising of Acquity LC and Thermo TSQ-Ultra) and the % active ingredient remaining after rainfall determined by dividing the quantity of AZ on each leaf after rainfall by that before rainfall.

TABLE 3

| Treatment | % azoxystrobin remaining on Leaves after rainfall |
| --- | --- |
| Azoxystrobin SC | 3.1 |
| Azoxystrobin SC + 0.003% | 11.0 |

TABLE 3-continued

| Treatment | % azoxystrobin remaining on Leaves after rainfall |
| --- | --- |
| styrene maleimide co-polymer Azoxystrobin SC + 0.006% styrene maleimide co-polymer | 5.6 |
| Azoxystrobin SC + 0.06% styrene maleimide co-polymer | 15.9 |
| Azoxystrobin SC + 0.12% styrene maleimide co-polymer | 17.3 |
| Azoxystrobin SC + 0.30% styrene maleimide co-polymer | 32.2 |

EXAMPLE 6

Preparation of a Built-In Formulation

Formulations containing the styrene maleimide copolymer were prepared by the substitution of water from a typical SC [example compositions of which are given below]. These were prepared using standard preparation methods. As is common in suspension concentrate formulations the active ingredients were bead milled to improve colloidal stability to a size of around 1-2 microns and added as a millbase, those skilled in the art will appreciate the addition of dispersants will increase the efficiency of the milling step. During addition of these components the form the polymer containing SC the formulation was mixed under high shear in a jacketed vessel at 10° C. for 10 minutes. The output was free flowing suspension concentrates.

TABLE 4

| Component | Order of addition | Quantity in (g/L) | Quantity in (g/L) |
| --- | --- | --- | --- |
| Azoxystrobin | 3 | 83 | 83 |
| Cyproconazole | 4 | 33 | 33 |
| Styrene malemide copolymer | 2 | 340 | 120 |
| Kelzan ™ | 5 | 2 | 2 |
| Water make-up | 1 | make-up to 1 litre | make-up to 1 litre |

EXAMPLE 7

Rainfastness of an azoxystrobin 200 g/l SC when mixed with a styrene maleimide-containing tank-mix adjuvant.

The example demonstrates that the styrene malemide copolymer can be combined with commercial tank-mix adjuvants to form emulsions which retains their rainfastness properties on spray tank dilution. Those skilled in the art will recognise such a composition would make a powerful tank mix adjuvant.

Preparation of Mix 1

Nimbus™ oil (6.0 ml) was added to a dispersion of Nanotope™ 26 SO50 WA50-30 (4.5 ml) in water (5.5 ml). The resulting mixture was rolled overnight.

Preparation of Mix 2

Nimbus™ oil (3.0 ml) was added to a dispersion of Nanotope™ 26 SO50 WA50-30 (4.5 ml) in water (2.0 ml). The resulting mixture was rolled overnight.

Preparation of Mix 3

Nimbus™ oil (5.0 ml) was added to a dispersion of Nanotope™ 26 SO50 WA50-30 (2.0 ml) in water (3.0 ml). The resulting mixture was rolled overnight.

The rainfastness study was conducted in the same manner as Example 2. Spray dilutions of 80 l/ha were prepared, comprising azoxystrobin SC at 300 ml/ha and the other components at the rate stated in the table below.

TABLE 5

| Treatment | % AI Remaining on Leaves after Rainfall | Standard Deviation |
| --- | --- | --- |
| Azoxystrobin SC + 0.6 l/ha Nimbus | 7 | 6.1 |
| Azoxystrobin SC + 0.6 L/ha Nimbus + 450 ml/ha Nanotope ™ 26 SO50 WA50-30 | 44 | 11.0 |
| Azoxystrobin SC + 1.6 l/ha Tankmix 1 | 40 | 24.7 |
| Azoxystrobin SC + 0.7 l/ha Tankmix 1 | 47 | 19.4 |
| Azoxystrobin SC + 0.95 l/ha Tankmix 2 | 72 | 8.2 |
| Azoxystrobin SC + 0.7 l/ha Tankmix 2 | 51 | 6.5 |

EXAMPLE 8

Improved rainfastness of izopyrazam with styrene maleimide copolymer on soya.

This study demonstrates that the addition of styrene malemide copolymer can reduce the loss of an active ingredient from a leaf surface during rainfall.

A range of substrates could have been used in this test but the chosen material in this example was soya leaf; soya, *Glycine Max* (Williams variety), was grown for 4 weeks in 4 inch pots with the top 2 tri-foliates used in the study. The leaves were mounted, using double sided tape, to flat tiles (30 cm by 30 cm) at an even spacing of 6 leaves per tile.

A deposition solution was then prepared at a concentration which could be used under commercial application conditions. In this case 0.25 g of an isopyrazam SC formulation (containing 250 g/l isopyrazam) was added to 99.58 g water as the control sample whilst the effect of the styrene malemide co-polymer was determined by creating a similar sample in which 0.5 g of the water was replaced by styrene malemide co-polymer.

Twenty 0.2 μl droplets were applied to each substrate using a micro applicator. The substrate was allowed to dry for 2 hours. After the drying period, one board containing 6 leaves per treatment was 'rained on', at 10 mm/hour for one hour while the other board was sampled by washing each leaf with 30 ml of acetonitrile (Sigma Aldrich) with gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 30 ml acetonitrile for 20 seconds).

The quantities of izopyrazam in the acetonitrile solutions were determined by mass spectrometry using a Waters Acquity UPLC and Thermo TSQ Quantum Ultra Triple Quadrupole MS Instrument or just LC/MS/MS.
Column:
Phase Kinetex C18
Length (mm) 50
Internal diameter (mm) 3.0
Particle Size (μm) 2.6

For all tests, the % active ingredient remaining after rainfall determined by dividing the quantity of izopyrazam on each leaf after rainfall by that before rainfall, leading to the following results:
Izopyrazam SC alone: after rainfall, 47% isopyrazam remained on the leaves.

Whereas: Izopyrazam SC+styrene malemide copolymer: after rainfall 84% isopyrazam remained on the leaves.

Clearly the styrene malemide co-polymer has dramatically improved the rainfastness of the isopyrazam.

EXAMPLE 9

Improved rainfastness of Helios™ SC with styrene maleimide copolymer on soya.

This study demonstrates that the addition of styrene malemide copolymer can reduce the loss of a model active ingredient (AI) from a leaf surface during rainfall. Helios SC is a UV tracer commonly used as a model for an AI, containing particles of 2,2'-(2,5-thiophenediyl)bis(5-tert-butylbenzoxazole).

A range of substrates could be used in this test but the chosen material in this example was soya leaf; soya, *Glycine Max* (Williams variety), was grown for 4 weeks in 4 inch pots with the top 2 tri-foliates used in the study. The leaves were mounted, using double sided tape, to flat tiles (30 cm by 30 cm) at an even spacing of 6 leaves per tile.

A deposition solution was then prepared at a concentration which could be used under commercial application conditions. In this case 0.181 g of a Helios™ SC formulation (containing 500 g/l 2,2'-(2,5-thiophenediyl)bis(5-tert-butylbenzoxazole)) was added to 99.684 g water as the control sample whilst the effect of the styrene malemide co-polymer was determined by creating a similar sample with 0.5 g of the water replaced by styrene malemide co-polymer.

Twenty 0.2 µl droplets were applied to each substrate using a micro applicator. The substrate was allowed to dry for 2 hours. After the drying period, one board containing 6 leaves per treatment was 'rained on', at 10 mm/hour for one hour while the other board was sampled by washing each leaf with 30 ml of acetonitrile (Sigma Aldrich) with gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 30 ml acetonitrile for 20 seconds).

The quantities of 2,2'-(2,5-thiophenediyl)bis(5-tert-butylbenzoxazole) in the acetonitrile solutions were determined via fluorimetry (Tecan M200 Pro, emission wavelength 429 mm) and the % active ingredient remaining after rainfall was determined by dividing the quantity of 2,2'-(2,5-thiophenediyl)bis(5-tert-butylbenzoxazole) on each leaf after rainfall by that before rainfall, leading to the following results:

Helios SC alone: after rainfall 41% 2,2'-(2,5-thiophenediyl)bis(5-tert-butylbenzoxazole) remained on the leaves.

Whereas Hellos™ SC+styrene malemide copolymer: after rainfall 78% 2,2'-(2,5-thiophenediyl)bis(5-tert-butylbenzoxazole) remained on the leaves.

Clearly the styrene malemide co-polymer has dramatically improved the rainfastness of the model AI.

EXAMPLE 10

Improved Rainfastness of cyantraniliprole with styrene maleimide copolymer on soya.

This study demonstrates that the addition of styrene malemide copolymer can reduce the loss of an active ingredient from a leaf surface during rainfall.

A range of substrates can be used in this test with the chosen material in this example being a soya leaf. Herein the soya, *Glycine Max* (Williams variety), was grown for 4 weeks in 4 inch pots with the top 2 tri-foliates used in the study. The leaves were mounted using double sided tape to flat tiles (30 cm by 30 cm) at an even spacing of 6 leaves per tile.

A deposition solution was then prepared at the concentration which would be used under commercial application conditions. In this case 0.12 g of cyantraniliprole technical was added to 99.82 g water for the control and the effect of the styrene malemide co-polymer determined by creating a similar sample with 0.5 g of the water replaced by styrene malemide co-polymer.

Twenty 0.2 µl droplets were applied to each substrate using a micro applicator. The substrate was allowed to dry for 2 hours. After the drying period one board containing 6 leaves per treatment were 'rained on', at 10 mm/hour for one hour while the other board was sampled by washing each leaf with 30 mls of acetonitrile (Sigma Aldrich) and gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 20 ml acetonitrile for 20 seconds).

The quantities of cyantraniliprole in the acetonitrile solutions determined by mass spectrometry using a Waters Acquity UPLC and Thermo TSQ Quantum Ultra Triple Quadrupole MS Instrument or just LC/MS/MS.

Column:
Phase Ace C18
Length (mm) 50
Internal diameter (mm) 3.0
Particle Size (µm) 3 and the % active ingredient remaining after rainfall determined by dividing the quantity of cyantraniliprole on each leaf after rainfall by that before rainfall.

Cyantraniliprole: 2% cyantraniliprole remained on the leaves.

Cyantraniliprole+styrene malemide copolymer: 45% cyantraniliprole remained on the leaves.

EXAMPLE 11

Improved rainfastness of chlorothalonil with styrene maleimide copolymer on soya.

This study demonstrates that the addition of styrene malemide copolymer can reduce the loss of an active ingredient from a leaf surface during rainfall.

A range of substrates can be used in this test with the chosen material in this example being a soya leaf. Herein the soya, *Glycine Max* (Williams variety), was grown for 4 weeks in 4 inch pots with the top 2 tri-foliates used in the study. The leaves were mounted using double sided tape to flat tiles (30 cm by 30 cm) at an even spacing of 6 leaves per tile.

A deposition solution was then prepared. In this case 3.6 g of a chlorothalonil SC formulation (containing 720 g/l chlorothalonil) was added to 97.3 g water for the control and the effect of the styrene malemide co-polymer determined by creating a similar sample with 0.5% w/w of the water replaced by styrene malemide co-polymer.

Twenty 0.2 µl droplets were applied to each substrate using a micro applicator. The substrate was allowed to dry for 2 hours. After the drying period one board containing 6 leaves per treatment were 'rained on', at 15 mm/hour for one hour while the other board was sampled by washing each leaf with 15 ml of acetonitrile (Sigma Aldrich) and gentle agitation for 20 seconds. The rainfall was simulated using a rain tower which combines the rate of water flow and shutter opening to achieve the target intensity of rainfall. The rain tower was positioned such that the droplets reached their terminal velocity before hitting the target surface. After the raining period, the 'rained on' leaves were washed using the same protocol (gentle agitation in 15 ml acetonitrile for 20 seconds).

The quantities of chlorothalonil in the acetonitrile solutions determined via LCMS (Thermo TSQ Quantum LC/MS/MS, Column 845) and the percent active ingredient remaining after rainfall was determined by dividing the quantity of chlorathalonil on each leaf after rainfall by that before rainfall.

Chlorothalonil SC: 19% chlorathalonil remained on the leaves.

Chlorothalonil SC™+styrene malemide copolymer: 93% chlorathalonil remained on the leaves.

The invention claimed is:

1. A composition comprising:
   (i) an aqueous continuous phase;
   (ii) a first dispersed phase dispersed in (i) which is particles with themselves comprise a styrene-maleimide co-polymer; and
   (iii) a second dispersed phase dispersed in (i) which is either droplets comprising an oil, is suspended solid particles, or is suspended capsules and wherein the second dispersed phase further comprises an agrochemical wherein the agrochemical is either an oil or is dissolved in oil, or is the suspended solid particles, or is present within the suspended capsules.

2. A composition as claimed in claim 1, where the agrochemical is an herbicide, a fungicide, or an insecticide.

3. A composition as claimed in claim 2, where the agrochemical is a fungicide or an insecticide.

4. A composition as claimed in claim 3, wherein the agrochemical is a strobilurin.

5. A composition as claimed in claim 1, where the concentration of the agrochemical is from 5% to 40% by weight.

6. A composition as claimed in claim 4, which further comprises a triazole fungicide.

7. A Composition as claimed in claim 6, where the total agrochemical concentration is from 55 to 40% by weight.

8. A composition as claimed in claim 1, where the second dispersed phase is droplets of an oil adjuvant.

9. A composition as claimed in claim 1, where the co-polymer has an anhydride monomer content which is from 15 to 50 mol %.

10. A composition as claimed in claim 1, where the weight averaged molecular weight of the styrene-maleimide co-polymer is form 4,000 to 500,000 g/mole.

11. A composition as claimed in claim 1, where the styrene-maleimide copolymer is of formula (I)

I where m is from 250 to 800; and n is from 100 to 400.

12. A composition as claimed in claim 11, where m is from 559 to 575; and n is from 200 to 225.

13. A composition as claimed in claim 11 where the concentration of the co-polymer is from 2 to 50% by weight.

* * * * *

UNITED STATES PATENT AND TRADEMARK OFFICE
CERTIFICATE OF CORRECTION

PATENT NO. : 10,085,442 B2
APPLICATION NO. : 15/302242
DATED : October 2, 2018
INVENTOR(S) : John Henry Nettleton-Hammond et al.

Page 1 of 1

It is certified that error appears in the above-identified patent and that said Letters Patent is hereby corrected as shown below:

In the Claims

Claim 7 Column 14, Line 11, '55' should read --5%--.

Claim 12 Column 14, Line 34, '559' should read --550--.

Signed and Sealed this
Third Day of November, 2020

Andrei Iancu
*Director of the United States Patent and Trademark Office*